(12) United States Patent
Kunzemann (10) Patent No.: US 10,709,087 B2
(45) Date of Patent: Jul. 14, 2020

(54) WILD ROCKET VARIETY 'JOLIZIA'

(71) Applicant: Enza Zaden Beheer B.V., Enkhuizen (NL)

(72) Inventor: Olaf Kunzemann, Dannstadt-Schauernheim (DE)

(73) Assignee: Enza Zaden Beheer B.V., Enkhuizen (NL)

( * ) Notice: Subject to any disclaimer, the term of this patent is extended or adjusted under 35 U.S.C. 154(b) by 53 days.

(21) Appl. No.: 16/150,201

(22) Filed: Oct. 2, 2018

(65) Prior Publication Data
US 2019/0098856 A1 Apr. 4, 2019

Related U.S. Application Data

(60) Provisional application No. 62/568,166, filed on Oct. 4, 2017.

(51) Int. Cl.
*A01H 6/20* (2018.01)
*A01H 5/12* (2018.01)

(52) U.S. Cl.
CPC .............. *A01H 6/205* (2018.05); *A01H 5/12* (2013.01)

(58) Field of Classification Search
None
See application file for complete search history.

(56) References Cited

U.S. PATENT DOCUMENTS

| | | |
|---|---|---|
| 5,304,719 A | 4/1994 | Segebart |
| 5,367,109 A | 11/1994 | Segebart |
| 5,523,520 A | 6/1996 | Hunsperger et al. |
| 5,763,755 A | 6/1998 | Carlone |
| 5,850,009 A | 12/1998 | Kevern |
| 8,507,760 B2 | 8/2013 | Kunzemann |
| 9,474,245 B2 | 10/2016 | Kunzemann |
| 9,968,059 B2 | 5/2018 | Kunzemann |
| 2012/0066788 A1 | 3/2012 | Kunzemann |
| 2012/0192303 A1 | 7/2012 | Knerr |
| 2015/0218580 A1 | 8/2015 | Kunzemann |
| 2017/0196189 A1* | 7/2017 | Kunzemann ............. A01H 5/12 |
| 2017/0280669 A1* | 10/2017 | Carree ................. C12Q 1/6895 |

OTHER PUBLICATIONS

Bassett, M. J., "The Role of Leaf Shape in the Inheritance of Heading in Lettuce (*Lactuca sativa* L.)", Journal of the American Society for Horticultural Science, vol. 100, No. 2, 1975, pp. 104-105.

Bennetzen et al., "Approaches and Progress in the Molecular Cloning of Plant Disease Resistance Genes", Genetic Engineering, vol. 14, 1992, pp. 99-124.

CPVO Database, "CPVR Application 20092566 of Enza Zaden Beheer BV, filed on Nov. 30, 2009", 1 page.

De Bolle et al., "Antimicrobial Peptides from Mirabilis Jalapa and Amaranthus Caudatus: Expression, Processing, Localization and Biological Activity in Transgenic Tobacco", Plant Molecular Biology, vol. 31, 1996, pp. 993-1008.

(Continued)

*Primary Examiner* — Ashley K Buran (74) *Attorney, Agent, or Firm* — Morrison & Foerster LLP (57) ABSTRACT

New wild rocket variety designated 'Jolizia' is described. 'Jolizia' is a wild rocket variety exhibiting stability and uniformity.

13 Claims, 4 Drawing Sheets

(4 of 4 Drawing Sheet(s) Filed in Color)

(56) References Cited

OTHER PUBLICATIONS

De Vries et al., "Numerical Morphological Analysis of Lettuce Cultivars and Species (*Lactuca* sect. Lactuca, Asteraceae)", Plant Systematics and Evolution, vol. 193, 1994, pp. 125-141.

Eshed et al., "Less-Than-Additive Epistatic Interactions of Quantitative Trait Loci in Tomato", Genetics, vol. 143, Aug. 1996, pp. 1807-1817.

Hall et al., "The Germination of Perennial Wall Rocket (*Diplotaxis tenuifolia* (L.) DC.) and Annual Garden Rocket (*Eruca sativa* Mill.) Under Controlled Temperatures", Plant Breeding and Seed Sciences, vol. 65, 2012, pp. 15-28.

Kraft et al., "Linkage Disequilibrium and Fingerprinting in Sugar Beet", Theor. Appl. Genet., vol. 101, 2000, pp. 323-326.

Michelmore et al., "Transformation of Lettuce (*Lactuca sativa*) Mediated by Agrobacterium Tumefaciens", Plant Cell Reports, vol. 6, 1987, pp. 439-442.

Nicoletti et al., "Diplotaxis Tenuifolia: Biology, Production and Properties", The European Journal of Plant Science and Biotechnology, vol. 1, No. 1, 2007, pp. 36-43.

Pang et al., "Expression of a Gene Encoding a Scorpion Insectotoxin Peptide in Yeast, Bacteria and Plants", Gene, vol. 116, 1992, pp. 165-172.

Ryder et al., "Inheritance and Epistasis Studies of Chlorophyll Deficiency in Lettuce", J. Amer. Soc. Hort. Sci., vol. 124, No. 6, 1999, pp. 636-640.

Ryder et al., "Lettuce Genetics: Inheritance, Linkage and Epistasis", J. Amer. Soc. Hort. Sci., vol. 117, No. 3, 1992, pp. 504-507.

Sikdar et al., "Plant Regeneration from Mesophyll Protoplasts of Diplotaxis Muralis, A Wild Crucifer", Plant Cell Reports, vol. 8, 1990, pp. 722-725.

Thomas et al., "Lettuce Production in the United States", Agriculture Handbook No. 221, Agricultural Research Service of the United States Department of Aquiculture, 1974, 3 pages.

Waycott et al., "Differentiation of Nearly Identical Germplasm Accessions by a Combination of Molecular and Morphologic Analyses", Genome, vol. 37, 1994, pp. 577-583.

Xinrun et al., "Genotypic Effects on Tissue Culture Response of Lettuce Cotyledons", J. Genet. & Breed., vol. 46, 1992, pp. 287-290.

\* cited by examiner

WILD ROCKET VARIETY 'JOLIZIA'

CROSS-REFERENCE TO RELATED APPLICATION

This application claims the benefit of U.S. Provisional Application No. 62/568,166, filed Oct. 4, 2017, which is hereby incorporated by reference in its entirety.

FIELD OF THE INVENTION

The present invention relates to the field of plant breeding. In particular, this invention relates to new wild rocket, *Diplotaxis tenuifolia* variety designated 'Jolizia'.

BACKGROUND OF THE INVENTION

Wild rocket, *Diplotaxis tenuifolia*, is a specialty leaf vegetable in the Brassicaceae family. Wild rocket is also known as arugula, sand mustard, sand rocket, Lincoln's weed, white rocket, and wall rocket. Wild rocket is a flowering plant that is a fast growing, cool season crop and flowers under long days and high temperatures. Unlike lettuce, arugula is not bitter and the branches are often used as an ingredient in salads.

Wild rocket is native to Europe and Western Asia. However, wild rocket may be found in temperate zones throughout much of the world. Wild rocket is an erect mustard-like plant with branching stems that can exceed half a meter in height. Yellow flowers grow from the top of branches of the stems, and the fruit is a straight, flat silique that can be up to five centimeters long. Wild rocket also has long leaves that can be lobbed, and the foliage is aromatic when crushed. Wild rocket generally grows in clumps on the ground in various habitats.

Wild rocket is an important and valuable vegetable crop. Accordingly, there is a need for new wild rocket varieties. In particular, there is a need for improved flat wild rocket varieties that are stable, high yielding, and agronomically sound.

SUMMARY OF THE INVENTION

In order to meet these needs, the present invention is directed to improved wild rocket varieties.

In one embodiment, the present invention is directed to wild rocket, *Diplotaxis tenuifolia*, seed designated as 'Jolizia', representative sample of seed having been deposited under NCIMB Accession Number 43274. In one embodiment, the present invention is directed to a *Diplotaxis tenuifolia* wild rocket plant and parts isolated therefrom produced by growing 'Jolizia' wild rocket seed. In another embodiment, the present invention is directed to a *Diplotaxis tenuifolia* plant and parts isolated therefrom having all the physiological and morphological characteristics of a *Diplotaxis tenuifolia* plant produced by growing 'Jolizia' wild rocket seed having NCIMB Accession Number 43274. In still another embodiment, the present invention is directed to an $F_1$ hybrid *Diplotaxis tenuifolia* wild rocket seed, plants grown from the seed, and a head isolated therefrom having 'Jolizia' as a parent, where 'Jolizia' is grown from 'Jolizia' wild rocket seed having NCIMB Accession Number 43274.

Wild rocket plant parts include wild rocket stems, wild rocket leaves, parts of wild rocket leaves, pollen, ovules, flowers, roots, cells, and the like. In another embodiment, the present invention is further directed to wild rocket stems, wild rocket leaves, parts of wild rocket leaves, flowers, pollen, and ovules, roots, or cells isolated from 'Jolizia' wild rocket plants. In another embodiment, the present invention is further directed to tissue culture of 'Jolizia' wild rocket plants, and to wild rocket plants regenerated from the tissue culture, where the plant has all of the morphological and physiological characteristics of 'Jolizia' wild rocket plants.

In still another embodiment, the present invention is further directed to packaging material containing 'Jolizia' plant parts. Such packaging material includes but is not limited to boxes, plastic bags, etc. The 'Jolizia' plant parts may be combined with other plant parts of other plant varieties.

In yet another embodiment, the present invention is further directed to a method of selecting wild rocket plants, by a) growing 'Jolizia' wild rocket plants where the 'Jolizia' plants are grown from wild rocket seed having NCIMB Accession Number 43274 and b) selecting a plant from step a). In another embodiment, the present invention is further directed to wild rocket plants, plant parts and seeds produced by the wild rocket plants where the wild rocket plants are isolated by the selection method of the invention. In another embodiment, the present invention is further directed to a method of breeding wild rocket plants by crossing a wild rocket plant with a plant grown from 'Jolizia' wild rocket seed having NCIMB Accession Number 43274. In still another embodiment, the present invention is further directed to wild rocket plants, wild rocket parts from the wild rocket plants, and seeds produced therefrom where the wild rocket plant is isolated by the breeding method of the invention.

In another embodiment, the present invention is directed to methods of producing an herbicide resistant wild rocket plant by introducing a gene conferring herbicide resistance into a wild rocket plant produced by growing 'Jolizia' wild rocket seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant wild rocket plants produced by such methods. In another embodiment, the present invention is directed to methods of producing a pest or insect resistant wild rocket plan by introducing a gene conferring pest or insect resistance into a wild rocket plant produced by growing 'Jolizia' wild rocket seed, and to pest or insect resistant wild rocket plants produced by such methods. In certain embodiments, the gene conferring pest or insect resistance encodes a *Bacillus thuringiensis* endotoxin. In another embodiment, the present invention is directed to methods of producing a disease resistant wild rocket plant by introducing a gene conferring disease resistance into a wild rocket plant produced by growing 'Jolizia' wild rocket seed, and to disease resistant wild rocket plants produced by such methods. In another embodiment, the present invention is directed to methods of producing a wild rocket plant with a value-added trait by introducing a gene conferring a value-added trait into a wild rocket plant produced by growing 'Jolizia' wild rocket seed, where the gene encodes a protein selected from a ferritin, a nitrate reductase, and a monellin. Certain embodiments are also directed to wild rocket plants having a value-added trait produced by such methods.

In another embodiment, the present invention is directed to methods of introducing a desired trait into wild rocket variety 'Jolizia', by: (a) crossing a 'Jolizia' plant, where a sample of 'Jolizia' wild rocket seed was deposited under NCIMB Accession Number 43274, with a plant of another wild rocket variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'Jolizia' plant to produce backcross progeny plants; (d) selecting for backcross progeny plants that have the desired trait and all of the physiological and morphological characteristics of wild rocket variety 'Jolizia'; and (e) repeating steps (c) and (d) two or more times in succession to produce selected third or higher backcross progeny plants that comprise the desired trait. Certain embodiments are also directed to wild rocket plants produced by such methods, where the plants have the desired trait and all of the physiological and morphological characteristics of wild rocket variety 'Jolizia'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

In another embodiment, the present invention provides for single gene converted plants of 'Jolizia'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage.

In a further embodiment, the present invention relates to methods for developing wild rocket plants in a wild rocket plant breeding program using plant breeding techniques including recurrent selection, backcrossing, pedigree breeding, restriction fragment length polymorphism enhanced selection, genetic marker enhanced selection, and transformation. Seeds, wild rocket plants, and parts thereof, produced by such breeding methods are also part of the invention.

In a further embodiment, the present invention relates to methods for developing wild rocket plants in a wild rocket plant breeding program using plant breeding techniques including recurrent selection, backcrossing, pedigree breeding, restriction fragment length polymorphism enhanced selection, genetic marker enhanced selection, and transformation. Seeds, wild rocket plants, and parts thereof, produced by such breeding methods are also part of the invention.

In addition to the exemplary aspects and embodiments described above, further aspects and embodiments will become apparent by reference by study of the following description.

DESCRIPTION OF THE DRAWINGS

The patent or application file contains at least one drawing executed in color. Copies of this patent or patent application publication with color drawings will be provided by the office upon request and payment of the necessary fee.

FIGS. 4A and 4B show a comparison between wild rocket varieties 'Jolizia' and 'Anastazia'.

DETAILED DESCRIPTION OF THE INVENTION

There are numerous steps in the development of novel, desirable wild rocket germplasm. Plant breeding begins with the analysis of problems and weaknesses of current wild rocket germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of wild rocket plant breeding is to develop new, unique, and genetically superior wild rocket varieties. A breeder can initially select and crosses two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial wild rocket varieties thus requires the development of parental wild rocket varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into wild rocket varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and "Carrots and Related Vegetable *Umbelliferae*," Rubatzky, V. E., et al. (1999).

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Bolting. The premature development of a flowering stalk, and subsequent seed, before a plant produces a food crop. Bolting is typically caused by late planting when temperatures are low enough to cause vernalization of the plants.

*Bremia lactucae.* An oomycete that causes downy mildew in leafy vegetables, such as lettuce and wild rocket, in cooler growing regions.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date.

Gene. As used herein, "gene" refers to a segment of nucleic acid. A gene can be introduced into a genome of a species, whether from a different species or from the same species, using transformation or various breeding methods.

*Hyaloperonospora parasitica.* An oomycete that causes downy mildew in leafy vegetables, such as wild rocket.

Maturity date. Maturity refers to the stage when the plants are of full size or optimum weight, in marketable form or shape to be of commercial or economic value.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Overview of the Variety 'Jolizia'

Figure 1:
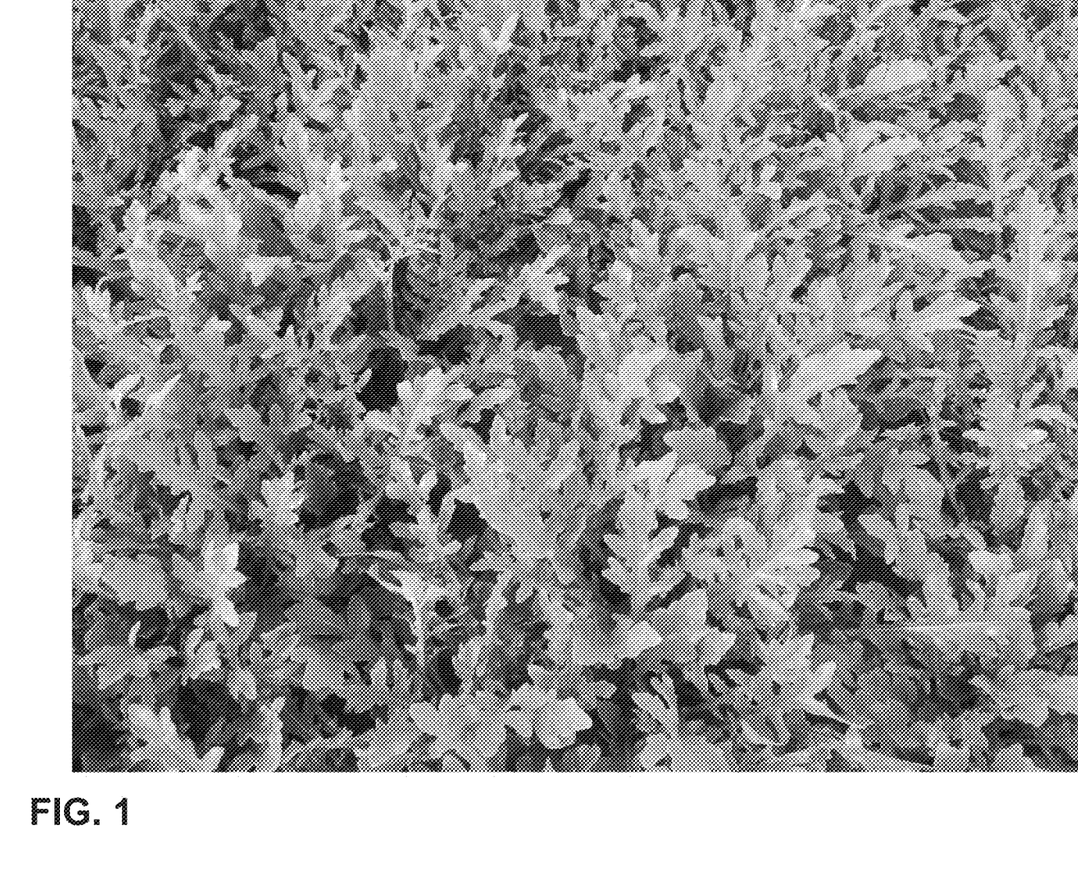
FIG. 1 shows an overhead view of wild rocket variety 'Jolizia'.
Figure 2:
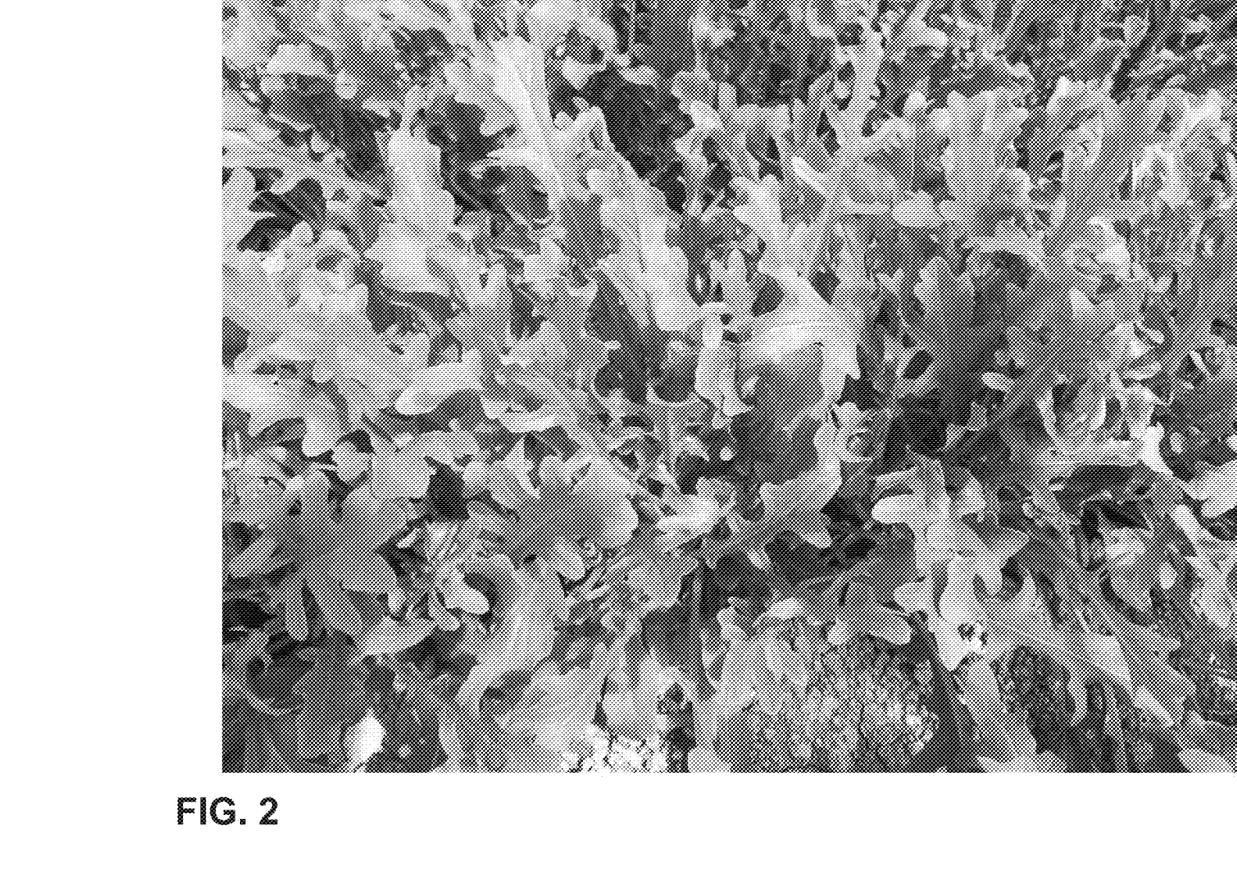
FIG. 2 shows a close-up view of wild rocket variety 'Jolizia'.
Figure 3:
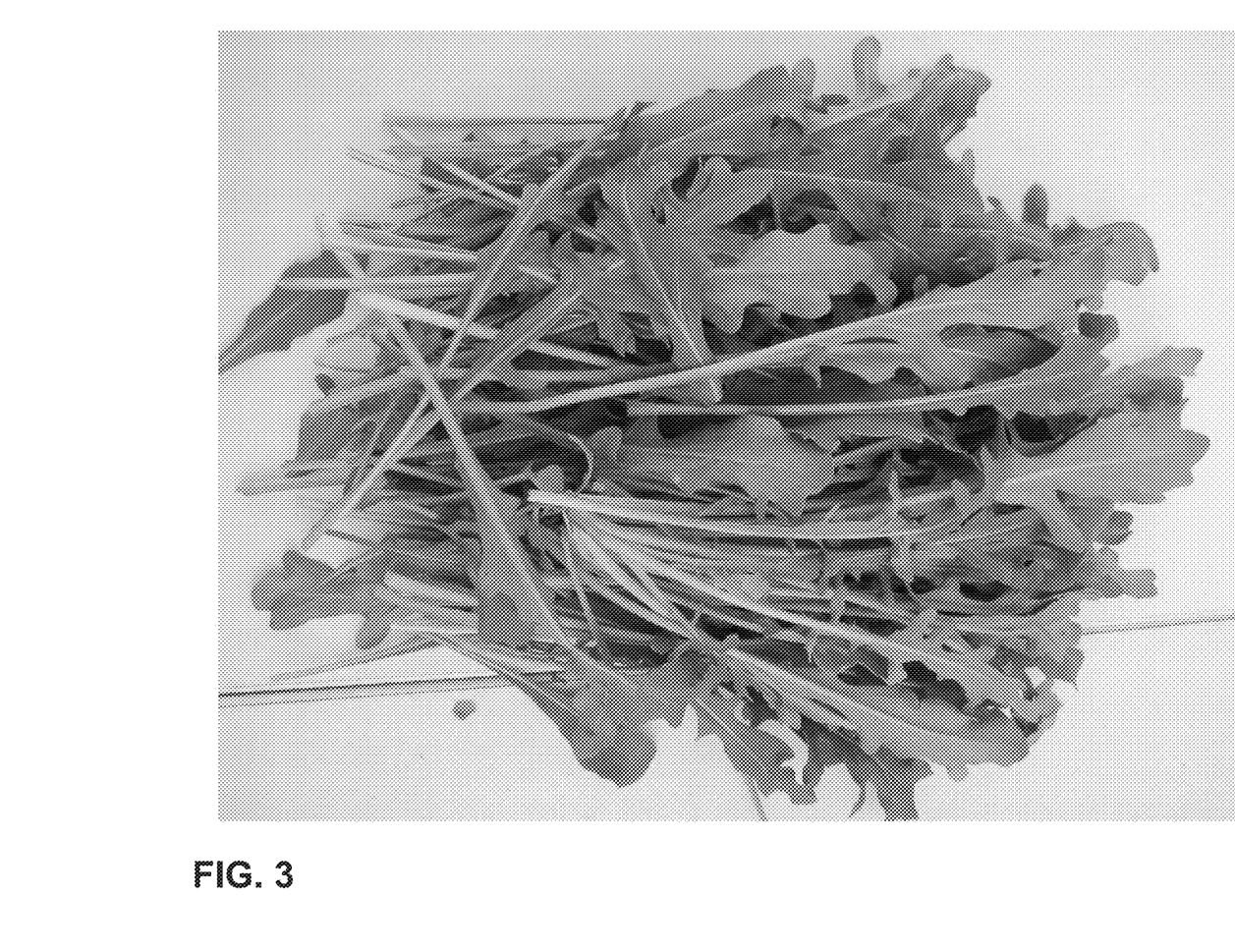
FIG. 3 shows leaves of wild rocket variety 'Jolizia'.

Wild rocket variety 'Jolizia' is a wild rocket variety suitable for greenhouse, open field, and tunnel production. Wild rocket variety 'Jolizia' is the result of numerous generations of plant selections chosen for its strong leaf division and intermediate resistance to downy mildew (Hyaloperonosporaparasitica). FIGS. 1-3 depict wild rocket variety 'Jolizia'.

The variety has shown uniformity and stability for the traits, within the limits of environmental influence for the traits. It has been increased with continued observation for uniformity. No variant traits have been observed or are expected in variety 'Jolizia'.

Objective Description of the Variety 'Jolizia'

Figure 4A:
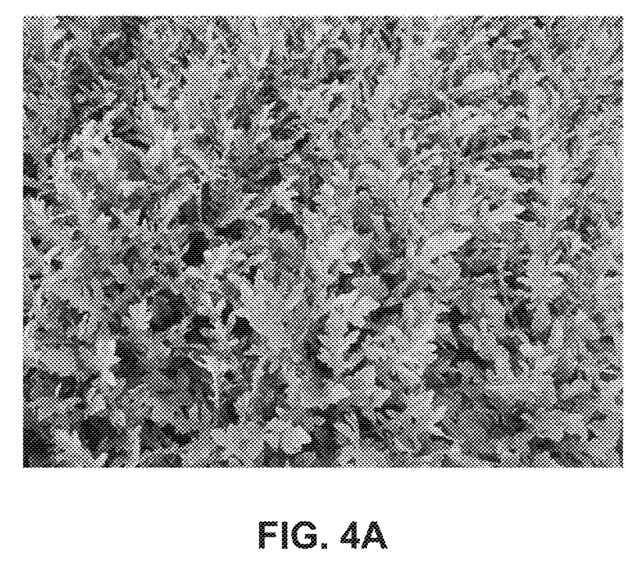
FIG. 4A shows wild rocket variety 'Jolizia'.
Figure 4B:
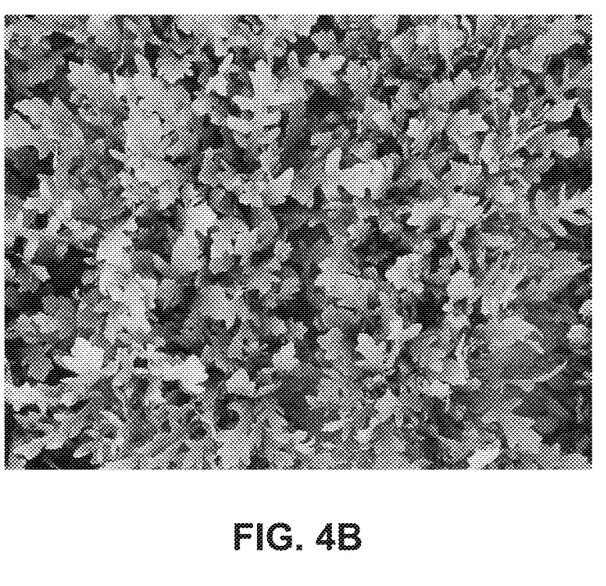
FIG. 4B shows wild rocket variety 'Anastazia'.

Wild rocket variety 'Jolizia' has the following morphologic and other characteristics:

Leaves:
Length: Short to medium
Width: Narrow to medium
Division: Strong
Secondary lobing: Medium; similar to variety 'Nature'
Plant:
Time of flowering: Medium; similar to variety 'Tiger'
Disease/Pest Resistance:
Downy Mildew (*Hyaloperonospora parasitica*): Intermediate resistance Comparison of 'Jolizia' to Commercial Wild Rocket Variety Table 1 below compares a characteristic of wild rocket variety 'Jolizia' with the wild rocket variety 'Anastazia'. Column 1 lists the characteristic, column 2 shows the characteristic for wild rocket variety 'Jolizia', and column 3 shows the characteristic for wild rocket variety 'Anastazia'. Further distinguishing features between 'Jolizia' and 'Anastazia' are apparent from the comparison of the two varieties depicted in FIGS. 4A and 4B.

TABLE 1

| Characteristic | 'Jolizia' | 'Anastazia' |
| --- | --- | --- |
| Leaf division | Strong | Weak |
| Leaf length | Short to medium | Short |
| Leaf width | Narrow to medium | Medium |
| Leaf secondary lobing | Medium | Absent or weak |
| Time of flowering | Medium | Late |

Further Embodiments

Gene Conversions

When the term "wild rocket plant" is used in the context of the present invention, this also includes any gene conversions of that variety. The term "gene converted plant" as used herein refers to those wild rocket plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental wild rocket plant which contributes the gene for the desired characteristic is termed the "nonrecurrent" or "donor parent." This terminology refers to the fact that the nonrecurrent parent is used one time in the backcross protocol and therefore does not recur. The parental wild rocket plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a wild rocket plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of wild rocket and regeneration of plants therefrom is well known and widely published. For example, reference may be had to Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., i Journal for the American Society for Horticultural Science, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a very high rate of success. Thus, another aspect of this invention is to provide cells which upon growth and differentiation produce wild rocket plants having the physiological and morphological characteristics of variety 'Jolizia'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a wild rocket plant by crossing a first parent wild rocket plant with a second parent wild rocket plant where the first or second parent wild rocket plant is a wild rocket plant of variety 'Jolizia'. Further, both first and second parent wild rocket plants can come from wild rocket variety 'Jolizia'. Thus, any such methods using wild rocket variety 'Jolizia' are part of the invention: selfing, backcrosses, hybrid production, crosses to populations, and the like. All plants produced using wild rocket variety 'Jolizia' as at least one parent are within the scope of this invention, including those developed from varieties derived from wild rocket variety 'Jolizia'. Advantageously, this wild rocket variety could be used in crosses with other, different, wild rocket plants to produce the first generation ($F_1$) wild rocket hybrid seeds and plants with superior characteristics. The variety of the invention can also be used for transformation where exogenous genes are introduced and expressed by the variety of the invention. Genetic variants created either through traditional breeding methods using wild rocket variety 'Jolizia' or through transformation of variety 'Jolizia' by any of a number of protocols known to those of skill in the art are intended to be within the scope of this invention.

The following describes breeding methods that may be used with wild rocket variety 'Jolizia' in the development of further wild rocket plants. One such embodiment is a method for developing variety 'Jolizia' progeny wild rocket plants in a wild rocket plant breeding program, by: obtaining the wild rocket plant, or a part thereof, of variety 'Jolizia', utilizing said plant or plant part as a source of breeding material, and selecting a wild rocket variety 'Jolizia' progeny plant with molecular markers in common with variety 'Jolizia' and/or with morphological and/or physiological characteristics selected from the characteristics listed in the section entitled "Objective description of the variety 'Jolizia'". Breeding steps that may be used in the wild rocket plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of wild rocket variety 'Jolizia' progeny wild rocket plants, by crossing variety 'Jolizia' with another wild rocket plant, thereby producing a population of wild rocket plants, which, on average, derive 50% of their alleles from wild rocket variety 'Jolizia'. A plant of this population may be selected and repeatedly selfed or sibbed with a wild rocket variety resulting from these successive filial generations. One embodiment of this invention is the wild rocket variety produced by this method and that has obtained at least 50% of its alleles from wild rocket variety 'Jolizia'. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes wild rocket variety 'Jolizia' progeny wild rocket plants containing a combination of at least two variety 'Jolizia' traits selected from those listed in the section entitled "Objective description of the variety 'Jolizia'"; or the variety 'Jolizia' combination of traits listed in the Summary of the Invention, so that said progeny wild rocket plant is not significantly different for said traits than wild rocket variety 'Jolizia' as determined at the 5% significance level when grown in the same environmental conditions. Using techniques described herein, molecular markers may be used to identify said progeny plant as a wild rocket variety 'Jolizia' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of wild rocket variety 'Jolizia' may also be characterized through their filial relationship with wild rocket variety 'Jolizia', as for example, being within a certain number of breeding crosses of wild rocket variety 'Jolizia'. A breeding cross is a cross made to introduce new genetics into the progeny, and is distinguished from a cross, such as a self or a sib cross, made to select among existing genetic alleles. The lower the number of breeding crosses in the pedigree, the closer the relationship between wild rocket variety 'Jolizia' and its progeny. For example, progeny produced by the methods described herein may be within 1, 2, 3, 4, or 5 breeding crosses of wild rocket variety 'Jolizia'.

As used herein, the term "plant" includes plant cells, plant protoplasts, plant cell tissue cultures from which wild rocket plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the wild rocket variety 'Jolizia' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of wild rocket variety 'Jolizia' were deposited on Nov. 16, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43274. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A wild rocket seed designated as 'Jolizia', representative sample of seed having been deposited under NCIMB Accession Number 43274.

2. A wild rocket plant produced by growing the seed of claim 1.

3. A plant part from the plant of claim 2.

4. The plant part of claim 3 wherein said part is a stem, a leaf, or a portion thereof.

5. A wild rocket plant having all the physiological and morphological characteristics of the wild rocket plant of claim 2.

6. A plant part from the plant of claim 5.

7. The plant part of claim 6, wherein said part is a stem, a leaf, or a portion thereof.

8. An $F_1$ hybrid wild rocket plant having 'Jolizia' as a parent where 'Jolizia' is grown from the seed of claim 1.

9. A pollen grain or an ovule of the plant of claim 2.

10. A tissue culture of the plant of claim 2.

11. A wild rocket plant regenerated from the tissue culture of claim 10, wherein the plant has all of the morphological and physiological characteristics of a wild rocket plant produced by growing seed designated as 'Jolizia', representative sample of seed having been deposited under NCIMB Accession Number 43274.

12. A method of making wild rocket seeds, said method comprising crossing the plant of claim 2 with another wild rocket plant and harvesting seed therefrom.

13. A method of making wild rocket variety 'Jolizia', said method comprising selecting seeds from the cross of one 'Jolizia' plant with another 'Jolizia' plant, a sample of 'Jolizia' wild rocket seed having been deposited under NCIMB Accession Number 43274.

* * * * *